United States Patent
Greenberg (10) Patent No.: US 6,514,201 B1
(45) Date of Patent: Feb. 4, 2003

(54) VOICE-ENHANCED DIAGNOSTIC MEDICAL ULTRASOUND SYSTEM AND REVIEW STATION

(75) Inventor: Jeffrey M. Greenberg, Palo Alto, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/239,271

(22) Filed: Jan. 29, 1999

(51) Int. Cl.$^7$ ................................................ A61B 8/00
(52) U.S. Cl. ........................................................ 600/437
(58) Field of Search ................................ 600/407, 437, 600/440–447; 704/256, 257, 235, 260; 345/8, 418; 73/620–626; 705/2

(56) References Cited

U.S. PATENT DOCUMENTS

| | | |
|---|---|---|
| 4,516,207 A | 5/1985 | Moriyama et al. |
| 4,819,271 A | 4/1989 | Bahl et al. |
| 5,146,439 A | 9/1992 | Jachmann et al. |
| 5,377,303 A | 12/1994 | Firman |
| 5,544,654 A * | 8/1996 | Murphy et al. .............. 600/443 |
| 5,553,620 A | 9/1996 | Snider et al. |
| 5,581,460 A | 12/1996 | Kotake et al. |
| 5,581,657 A | 12/1996 | Lyon |
| 5,592,374 A | 1/1997 | Fellegara et al. |
| 5,605,153 A | 2/1997 | Fujioka et al. |
| 5,611,060 A | 3/1997 | Belfiore et al. |
| 5,619,991 A | 4/1997 | Sloane |
| 5,636,631 A | 6/1997 | Waitz et al. |
| 5,651,099 A | 7/1997 | Konsella |
| 5,655,084 A | 8/1997 | Pinsky et al. |
| 5,659,665 A | 8/1997 | Whelpley, Jr. |
| 5,660,176 A | 8/1997 | Iliff |
| 5,724,968 A | 3/1998 | Iliff |
| 5,740,801 A * | 4/1998 | Branson ..................... 128/920 |
| 5,748,191 A | 5/1998 | Rozak et al. |
| 5,758,322 A | 5/1998 | Rongley |
| 5,761,641 A | 6/1998 | Rozak et al. |
| 5,853,367 A | 12/1998 | Chalek et al. |
| 5,920,317 A * | 7/1999 | McDonald ................... 345/835 |
| 5,957,849 A * | 9/1999 | Munro ........................ 600/459 |
| 5,970,457 A | 10/1999 | Brant et al. |
| 5,971,923 A * | 10/1999 | Finger ......................... 600/437 |
| 6,031,526 A | 2/2000 | Shipp |
| 6,032,120 A * | 2/2000 | Rock et al. ..................... 705/2 |
| 6,083,167 A * | 7/2000 | Fox et al. .................... 600/439 |
| 6,159,150 A * | 12/2000 | Yale et al. ................... 600/437 |
| 6,238,344 B1 * | 5/2001 | Gamelsky et al. ........... 128/903 |

OTHER PUBLICATIONS

L&H PowerScribe for Radiology—Product Specifications and System Requirements, 2 pages (printed 2000).
The Eloquent Physician—The Document Creation Assistant, 2 pages (1999).
21$^{st}$ Century Eloquence—Voice Recognition Specialists, http://www.voicerecognition.com, 2 pages (1999).
IBM MedSpeak/Radiology—The Continuous Speech Recognition Solution for Radiology Dictation, http://fl.pair.com/voice/vms.htm, 7 pages (printed 2000).
L&H Clinical Report—Frequently Asked Questions, http://www.lhsl.com/clinicalreporter/faq.asp, 3 pages (printed 2000).
Ali Diagnostic Reporting, Nov. 24, 1997 (31 pages).

* cited by examiner

Primary Examiner—Marvin M. Lateef
Assistant Examiner—Ali M. Imam (57) ABSTRACT

The preferred embodiments described herein relate to voice-enhanced diagnostic medical ultrasound imaging systems and review stations as well as to voice-related user interfaces. With these preferred embodiments, a user can interact with an imaging system or review station by issuing verbal commands instead of using a mouse, keyboard, or other user interface that requires physical manipulation by the user. This provides a very user-friendly interface, especially to those users who have difficulty navigating complex window and menu hierarchies or who have trouble manipulating pointing devices. This also improves patient flow and provides a more efficient report generation system. Voice feedback can also be used to allow the imaging system or review station to better communicate with a user.

34 Claims, 8 Drawing Sheets

VOICE-ENHANCED DIAGNOSTIC MEDICAL ULTRASOUND SYSTEM AND REVIEW STATION

BACKGROUND

There are several steps involved in providing a diagnosis of a patient based on an ultrasound examination. First, the ultrasound examination is performed on an ultrasound imaging system. The images generated from this examination can then be digitally stored and reviewed by a physician on an ultrasound review station, which is typically coupled with an ultrasound imaging system though a network. The ultrasound review station can display images, text, and measurement and calculation data and can also be used to facilitate the production of ultrasound examination reports. Based on his analysis at the review station, the physician generates an ultrasound examination report to provide a diagnosis. Often, a physician will dictate his diagnosis onto an audio tape or recording system, and the diagnosis is later transcribed and entered into an ultrasound examination report. Alternatively, the diagnosis can be typed into the ultrasound imaging system.

To assist in the performance of an ultrasound examination, some ultrasound imaging systems allow voice control of some of the operations of the system. Typically, a voice recognition unit, which is either part of or separate from the ultrasound imaging system's processor, converts an incoming voice signal to a control signal using voice information stored in the voice recognition unit. To enhance recognition performance, U.S. Pat. No. 5,544,654, which is assigned to the assignee of the present invention, describes an ultrasound imaging system in which a subset of voice information is used based on the operating state of the ultrasound imaging system. Specifically, the ultrasound imaging system's processor provides the voice recognition unit with an indication of its operating state, and the voice recognition unit selects only the portions the voice information that are relevant to the operating state. Because the voice recognition unit makes the selection based on the provided indication of operating state, the voice recognition unit and processor must be synchronized to ensure proper selection, especially when the processor is shipped separately from the voice recognition unit and when the processor is updated without updating the voice recognition unit.

To assist the physician review ultrasound images at a review station, graphical user interfaces have been used to provide a more user-friendly environment for the physician. Typically, these graphical user interfaces have windows, menus, and buttons, and a visual focus manipulated by a pointing device such as a mouse, keyboard, or trackball. Ultrasound review stations often have so many functions that applications are divided into hierarchies of menus and sub-menus, dialogs and sub-dialogs, and windows and sub-windows. Although graphical user interfaces were intended to facilitate interaction with the review station, some users have difficulty finding the desired functionality in the complex windows and menu hierarchies. Some users also find it difficult to fluidly manipulate pointing devices that require click and double-click actions.

Finally, to reduce the time needed to produce an ultrasound examination report and to improve the overall diagnostic workflow for a patient, automatic transcription systems have been used, such as Medspeak from IBM, Clinical Reporter from Lernout & Hauspie, and Powerscribe from the MRC Group. These systems are stand-alone devices with specialized vocabularies and are not incorporated with the ultrasound imaging system or review station. Some transcription systems attempt to transcribe every word voiced by the physician. Because of limitations in current transcription technology, these systems often produce inaccurate transcriptions. To overcome this problem, some systems reduce the amount of automatic dictation that is needed by creating macros, which, when spoken, trigger a longer text to be inserted into the report. Although typically more accurate than automatic dictation systems, these systems also encounter recognition problems. To further enhance accuracy, some systems use inline-style macro displays, in which a proposed textual phrase is displayed to a user for acceptance. Because these systems only need to recognize the command to accept or reject the proposed textual phrase, recognition accuracy is increased. However, presenting proposed textual phrases to a user can be a time consuming process, especially if the user rejects several proposed phrases before reaching an acceptable phrase.

There is, therefore, a need for an improved diagnostic medical ultrasound imaging system and review station to overcome the problems described above.

SUMMARY

The present invention is defined by the following claims, and nothing in this section should be taken as a limitation on those claims.

By way of introduction, the preferred embodiments described below relate to voice-enhanced diagnostic medical ultrasound imaging systems and review stations as well as to voice-related user interfaces. With these preferred embodiments, a user can interact with an imaging system or review station by issuing verbal commands instead of using a mouse, keyboard, or other user interface that requires physical manipulation by the user. This provides a very user-friendly interface, especially to those users who have difficulty navigating complex window and menu hierarchies or who have trouble manipulating pointing devices. This also improves patient flow and provides a more efficient report generation system. Voice feedback can also be used to allow the imaging system or review station to better communicate with a user.

The preferred embodiments will now be described with reference to the attached drawings.

DETAILED DESCRIPTION OF THE PRESENTLY PREFERRED EMBODIMENTS

Voice Recognition Unit

Figure 1:
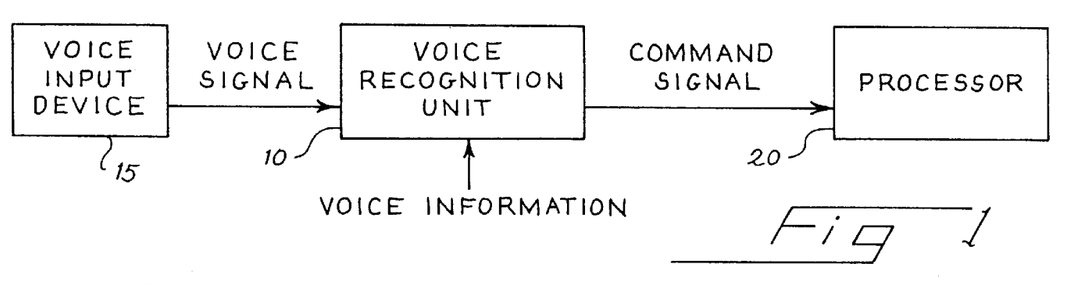
FIG. 1 is a block diagram illustrating an operation of a voice recognition unit of a preferred embodiment.

A voice recognition unit can be used to provide voiced commands to an ultrasound imaging system or review station, and FIG. 1 provides a block diagram of a voice recognition unit 10 of a preferred embodiment. As shown in FIG. 1, the voice recognition unit 10 is coupled with a voice input device 15 (such as a microphone) and a processor 20 of an ultrasound imaging system or review station. As used herein, the term "coupled with" means directly coupled with or indirectly coupled with through one or more components. It is preferred that the voice recognition unit 10 comprise a recognition engine (such as one available from Dragon Systems, IBM, Lernout & Hauspie, or Entropic Ltd.) and a voice technology software interface (such as SAPI 4.x from Microsoft Corp., SRAPI, JSAPI java from Sun Microsystems Corp., or SVAPI).

In regard to architecture, the voice recognition unit 10 can be separate from the processor 20, such as when the voice recognition unit 10 takes the form of software running on a separate processor. In one embodiment, the separate processor is a general-purpose computer directly coupled with the ultrasound imaging system or review station. For example, a general-purpose computer can be directly connected to an ultrasound imaging system and carried on the system cart, thereby appearing to a user to be integrated with the system. As described below, a separate processor can also be located in a server coupled with the ultrasound imaging system or review station through a network. In another preferred embodiment, some or all of the functionality of the voice control unit 10 is implemented with the ultrasound imaging system's or review station's processor 20.

For simplicity, the term "voice recognition unit" is used in the specification and claims to broadly refer to hardware and/or software components that use voice information to recognize an incoming voice signal from a voice input device 15 to generate and provide a command signal to a processor 20 of an ultrasound imaging system or review station. As used herein, the term "voice information" refers to data that correlates a set of voice signals (e.g., voiced commands from a user) with an associated set of respective command signals recognizable by the processor of the ultrasound imaging system or review station. The term "set" in the specification and claims refers to one or more than one element. In addition to providing this recognition profile, voice information can include engine usage information (e.g., percent of the CPU dedicated to recognition), user-adjustable recognition parameters (e.g., minimum volumes, timeouts to recognized complete and incomplete phrases), and a list of voice input devices and their capabilities that the user trained with and that the recognition profile is appropriate for. Voice information can also include user-specific voice commands and non-GUI user-specific voice parameters, such as preferred speak-back voice, dictation parameters, and dialog parameters. The recognition engine of the voice recognition unit 10 compares the incoming voice signal with the recognition profile of the voice information to determine which command signal should be sent to the processor 20. To enhance recognition performance, it is preferred that a finite-state-machine language description (e.g., Backus-Naurer) be used to provide the voice recognition unit 10 with various forms of legal speech and that a dictionary of synonyms be used to recognize equivalent voiced commands.

Also as used herein, the term "command signal" is used to refer to any signal that is recognizable by the processor 20 as an instruction to perform an operation or function performable by the processor 20 (e.g., the selection of a field, window, or monitor). In addition to controlling some aspect of the ultrasound imaging system or review station, a command signal can be a signal that provides the processor 20 with a text or other message. For example, the command signal can comprise a textual phrase that will be inserted into an ultrasound examination report.

Voice Information

Figure 2:
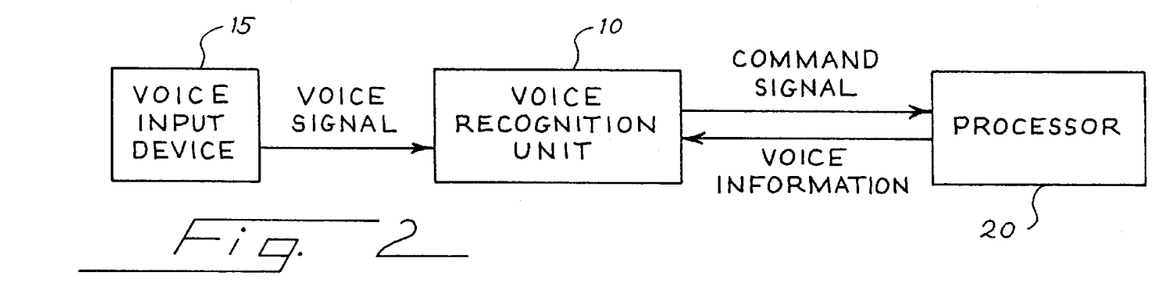
FIG. 2 is a block diagram illustrating a voice recognition unit of a preferred embodiment receiving voice information from an ultrasound imaging system or review station processor.

As described above, the voice recognition unit 10 uses voice information to generate a command signal in response to a voiced command from a user. Voice information can be provided to the voice recognition unit 10 by any appropriate source. In the preferred embodiment shown in FIG. 2, a server coupled with and integral with the ultrasound imaging system or review station processor 20 provides the voice information to the voice recognition unit 10. With this preferred embodiment, the processor 20 can create voice information containing only those voice and command signals that are relevant to the current operating state of the processor 20, thereby enhancing voice recognition. For example, if an ultrasound review station is currently being used to generate an ultrasound examination report for an obstetrics examination, the processor 20 can provide the voice recognition unit 10 with voice information containing only those voice and command signals commonly used with an obstetrics examination. Because the processor 20 provides voice information and not merely an indication of operating state, the processor 20 and voice recognition unit 10 can operate independently, thereby eliminating the problems encountered in prior system when the processor and voice recognition unit were not synchronized.

Figure 3:
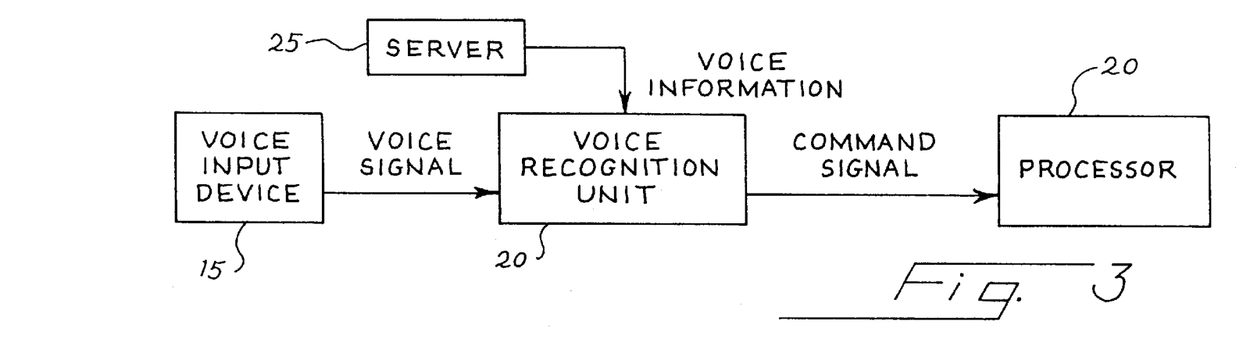
FIG. 3 is a block diagram illustrating a voice recognition unit of a preferred embodiment receiving voice information from a server.

The voice information can also be provided to the voice recognition unit 20 by a server 25 externally coupled with the voice recognition unit 20, as shown in FIG. 3. This preferred embodiment is particularly useful in a network environment in which the server 25 is coupled with several ultrasound imaging systems or review stations. In such an environment, voice information customized for a particular user is centrally located in the server 25. When that user identifies himself to a device on the network, the user's customized voice information is provided to the voice recognition unit of that device. This provides a coherent network environment in which commands are consistently recognized. If the user changes the voice information when using the device (such as when the user corrects a misidentified word), the centrally-stored voice information is updated as well. In this way, the user is not only provided with greater access to his customized voice information, but he is also given more opportunities to update the voice information to enhance recognition performance. If a user is using multiple ultrasound devices on the network simultaneously, the voice information that is accessed first or, alternatively, the voice information that is the most up-to-date can be used.

To select customized voice information (stored in an external server 25 or in a server integrated with the ultrasound imaging system or review station), the user can identify himself by providing non-verbal identification information, such as by typing his user name and password into a log-in screen. If the voice recognition unit 20 comprises a speaker identification engine (such as Keyware by Keyware Technologies or SpeakEZ Voice Print by T-Netix Inc.), the user can also identify himself by providing verbal identification information. For example, with a speaker identification engine, the voice recognition unit 20 can identify the user when he voices a command to the voice input device 15 or when he provides a voice sample to gain access to the ultrasound system or review station, as described in U.S. Pat. No. 6,129,671, which is hereby incorporated by reference and assigned to the assignee of the present application.

Applications

As described above, the voice recognition unit 10 can be implemented in either an ultrasound imaging system or an ultrasound review station to control the operation of the system or station. For example, by using the voice recognition unit 10 with an ultrasound review station, instructions to the review station can be given using voice commands instead of or in combination with using a mouse, keyboard, or other user interface that requires physical manipulation by the user. A verbal interface provides a user with a much more user-friendly interface, especially for those users who have difficulty finding the desired function in complex window and menu hierarchies or who have trouble manipulating pointing devices. With the voice recognition unit 10, a user can instruct the review station to view a desired report, worksheet, study list, or image. The user can also use voice commands to navigate through display information (e.g., "page up"), respond to visual requests (e.g., "press ok"), and perform operations (e.g., "zoom image 5"). The voice command can also be associated with multiple operations. For example, the command "use equation A to calculate birth weight" can trigger the ultrasound review system to perform the requested calculation and place the result into a particular section of an ultrasound examination report. Such operations can reference imaging, post-processing, and computational and calculation data.

The following is a description of specific implementations of methods that can be performed with a voice recognition unit. For simplicity, the following embodiments will be described in terms of an ultrasound review station. It is important to note that all of these implementation can also be implemented on an ultrasound imaging system and that one or more of these applications can be used in combination.

Figure 4:
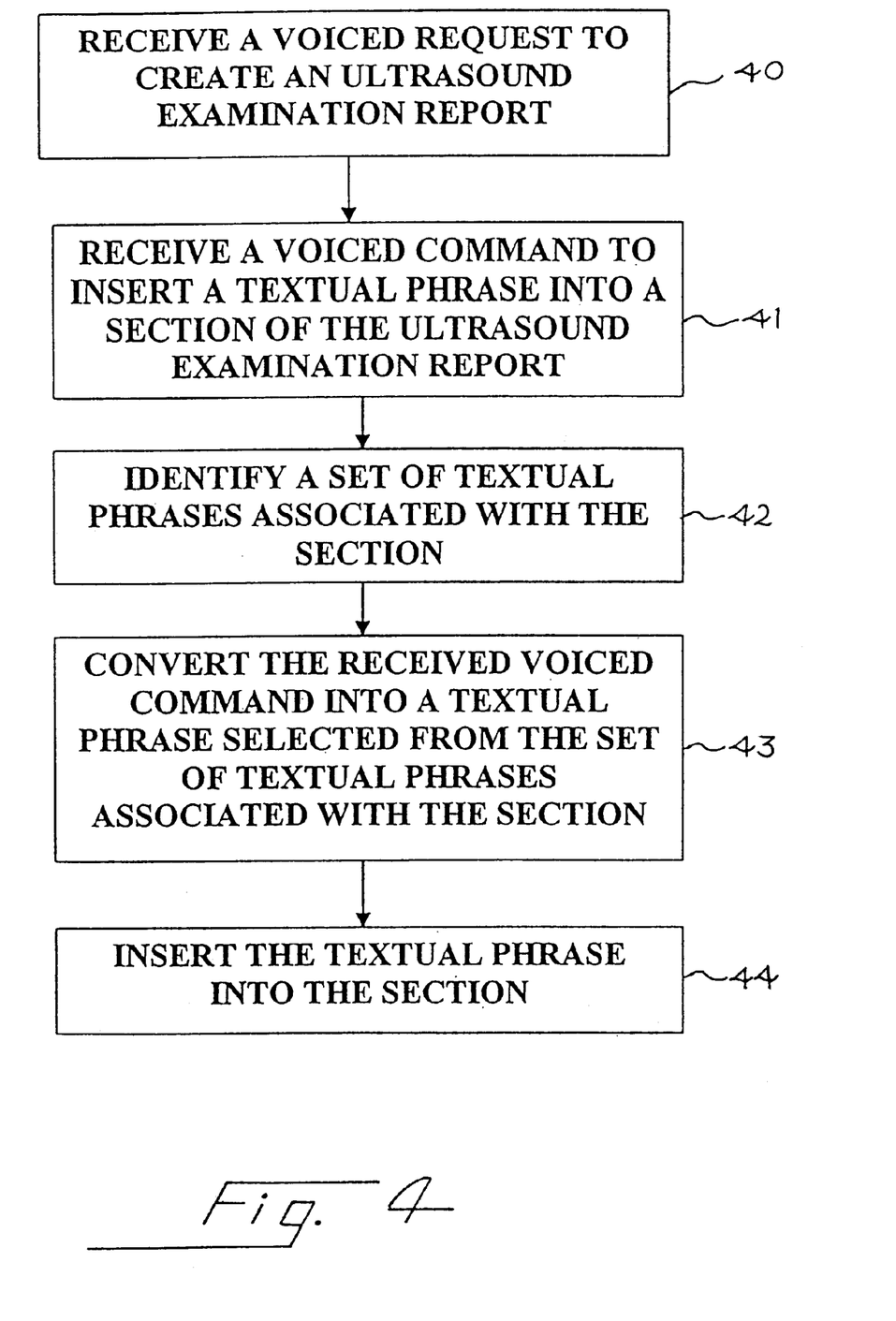
FIG. 4 is a flow chart of a preferred method for using voice commands to insert a textual phrase into a section of an ultrasound examination report.
Figure 5:
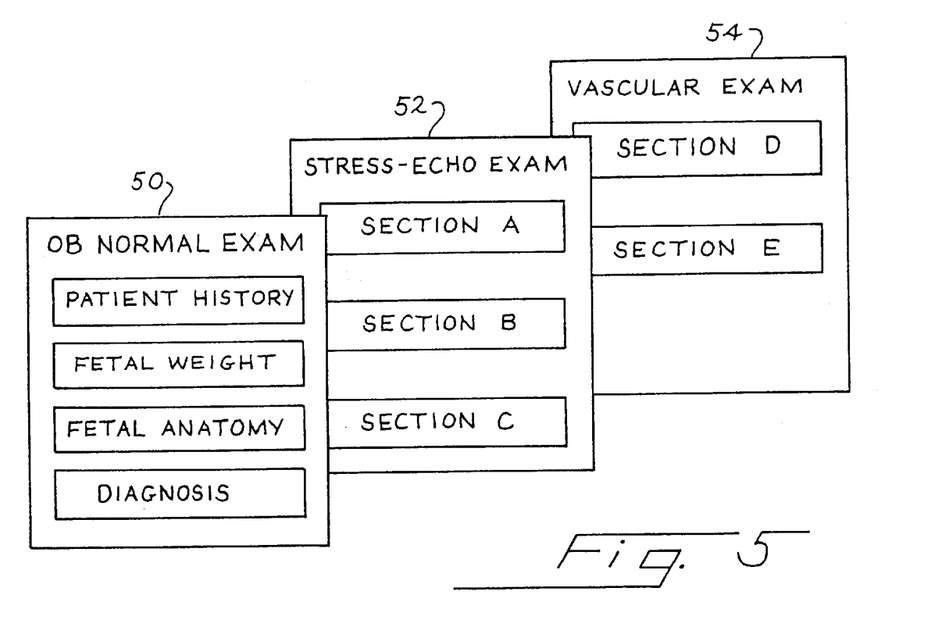
FIG. 5 is an illustration of several preferred ultrasound examination reports.

In one preferred embodiment, the voice recognition unit 10 implements a method for using voiced commands to insert a textual phrase into a section of an ultrasound examination report. As used herein, the term "phrase" refers to a string of one or more characters, such as one or more letters, words, numbers, or symbols, and the term "insert" refers to inserting, overwriting, replacing, and/or adding at a specified location. Such a method is illustrated in the flow chart of FIG. 4. The first step in this method is to receive a voice request to create an ultrasound examination report (40). As shown in FIG. 5, there are typically several types of ultrasound examination reports available to the user. Each report is associated with a particular type of ultrasound examination. For example, an ultrasound examination report can be used to provide information about a normal obstetrics examination 50, a stress-echo examination 52, or a vascular examination 54. Each report also has at least one section that will accept information from a user. For example, the normal obstetrics examination report 50 includes patient history, fetal weight, fetal anatomy, and diagnosis sections.

Figure 6:
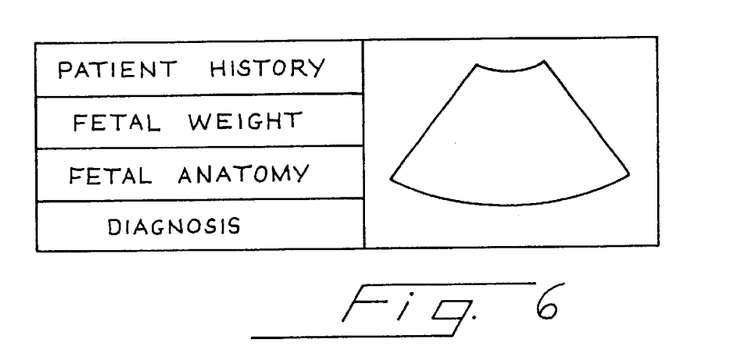
FIG. 6 is an illustration of a displayed ultrasound examination report of a preferred embodiment.

In response to the voiced request to create a particular ultrasound examination report, the ultrasound review station displays the report template to the user. For example, if the user requests a normal obstetrics examination report, the template with the sections associated with such a report is displayed to the user, as shown in FIG. 6. The user is also informed which section in the report is active (i.e., which section will received input from the user). For example, a cursor positioned in the diagnosis section would inform the user that the diagnosis section will receive input.

Figure 7:
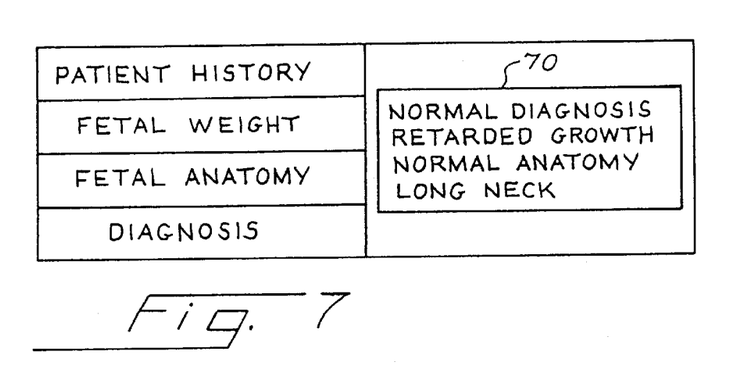
FIG. 7 is an illustration of a displayed ultrasound examination report of another preferred embodiment in which a menu of available commands is displayed along with the report.

Next, a voiced command is received from the user to insert a textual phrase into the active section (41). Preferably, the voiced command is a single word or short phrase that triggers a macro for the insertion of a longer textual phrase into the report. For example, the command "normal diagnosis" can be associated with the textual phrase "There is no evidence of abnormal development. The fetus is normal." To assist the user in selecting a command, the available voice commands for the active section can be provided to the user, for example, by displaying a menu of available commands for that section. In the example shown in FIG. 7, the menu 70 informs the user that the commands "normal diagnosis," "retarded growth," "normal anatomy," and "long neck" are available for the diagnosis section. In one preferred embodiment, the menu is automatically displayed to the user, while in another preferred embodiment, the menu is provided and/or removed in response to a verbal request from the user.

To increase recognition performance, each section of the report can be associated with a respective set of textual phrases. To convert the voiced command into a textual phrase, first the set of textual phrases associated with the active section is identified (42), and then the voiced command is converted into one of the textual phrases from the set (43). By basing the conversion on only those textual phrases associated with the active section instead of all available textual phrases, recognition performance is enhanced. Finally, the textual phrase is inserted into the section (44). This method can be used instead of or in conjunction with a pure transcription service.

Additionally, a user can voice commands to perform an editing operation (e.g., cut-and-paste) to the ultrasound examination report or to insert an ultrasound image into the report.

In another preferred embodiment, the voice recognition unit is used to place a marker on an ultrasound image displayed on a display device of an ultrasound review station. As used herein, the term "marker" is intended to broadly refer to any textual word or phase or any graphic that can be displayed on an ultrasound image displayed on a display device of an ultrasound imaging system or review station. A marker includes, but is not limited to, a word or phase used to identify anatomy and a geometric shape (such as a square or circle) used to identify a region of interest.

Figure 8:
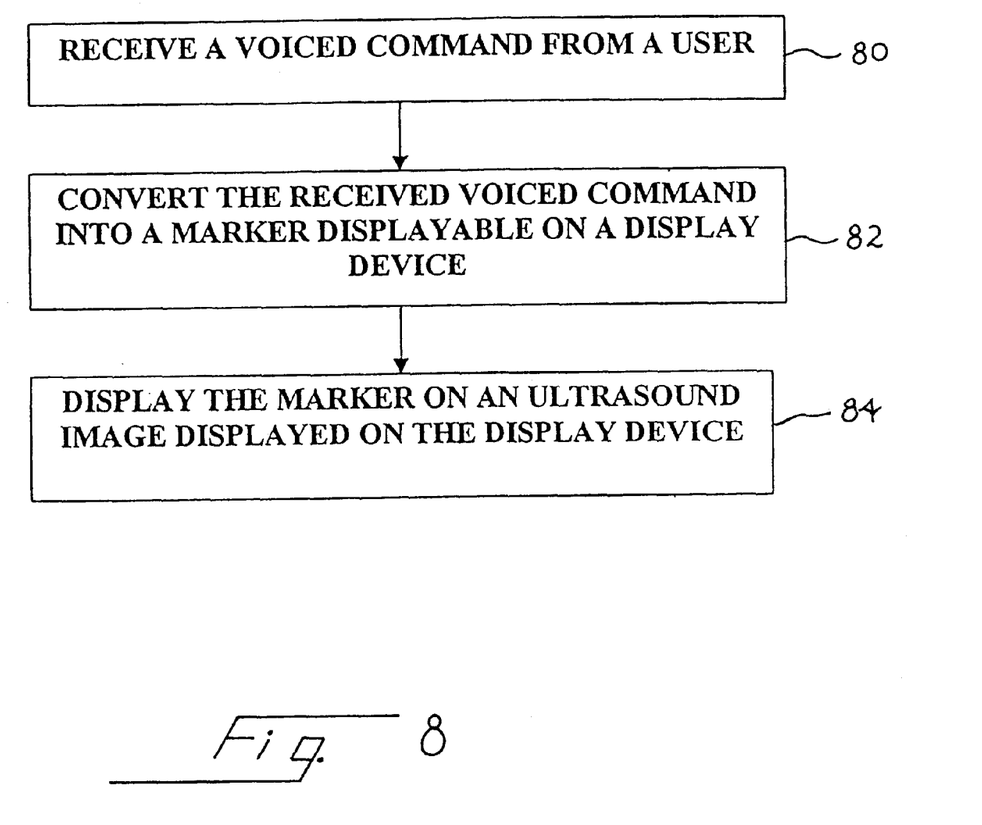
FIG. 8 is a flow chart of a preferred method for using voice commands to display a marker on an ultrasound image.
Figure 9:
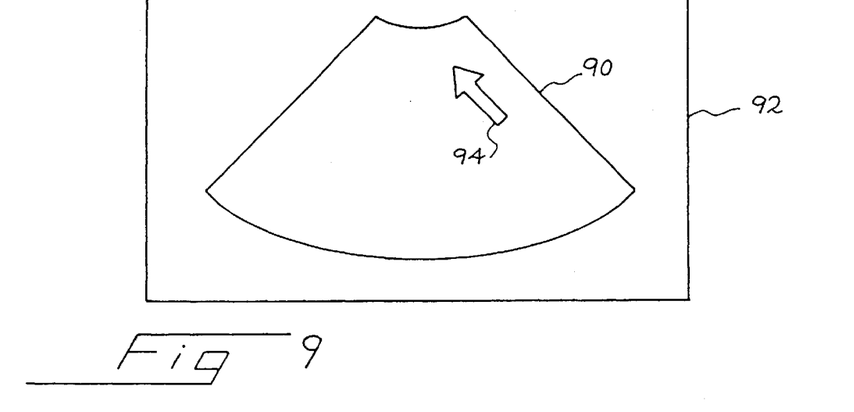
FIGS. 9–11 are illustrations of preferred displayed ultrasound images used in conjunction with the preferred method of the flow chart of FIG. 8.
Figure 10:
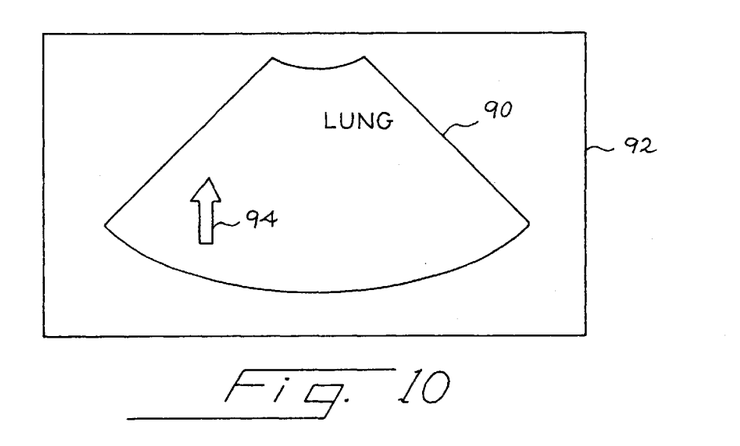
Figure 11:
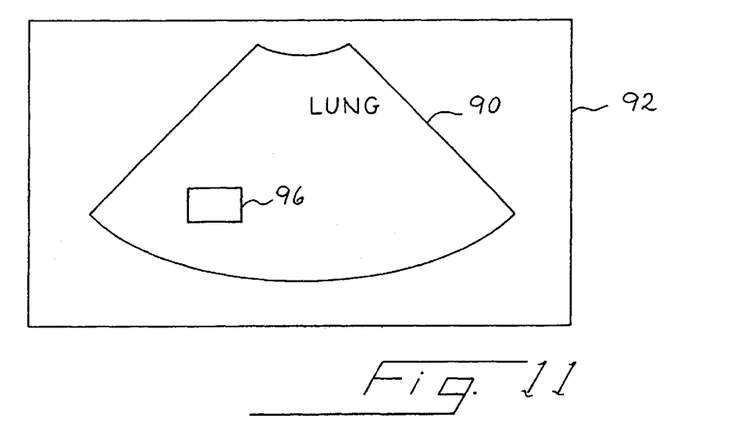

FIG. 8 is a flow chart of a preferred method for using voice commands to display a marker on an ultrasound image, which will be illustrated in conjunction with the ultrasound images shown in FIGS. 9–11. FIG. 9 is an illustration of an ultrasound image 90 displayed on a display device 92 of an ultrasound review station. When the user desires to place a marker on the ultrasound image 90, he positions a pointer 94 over the location on the ultrasound image 90 where he wishes to place the marker. After the pointer is positioned, the user issues a voice command to display the marker on the image (80). For example, if the user wishes to label the image 90 under the pointer 94 with the word "lung," he would issue a voiced command such as "lung." When voice commands are used for a plurality of applications, it is preferred to provide the system with a voiced command indicating that a subsequent voiced command will be associated with a marker. For example, the voiced command "label" can be given before every voiced command for a marker to inform the system that it should display the marker associated with the first subsequent voiced command. Alternatively, the voiced command "label on" can be given once, and all subsequent voiced commands can be converted to markers until the voiced command "label off" is given or until another command is issued that implicitly ends labeling.

Next, the received voiced command is converted into a marker displayable on the display device (82). In one embodiment, the received voiced command is compared to the system's entire voice information to determine which marker is associated with the voiced command. To improve recognition, it is preferred that only a subset of the voice information be used to convert the voiced command into a marker. Preferably, ultrasound images are classified by a study type, and only those markers associated with that study type are used to convert the voiced command into a marker. An indication of the study type can be provided with the image, or the system can analyze the image to determine the set of anatomical regions and the corresponding vocabulary.

After the voiced command is converted to a marker, the marker is displayed on the ultrasound image (84). As shown in FIG. 10, the word "lung" is displayed on the ultrasound image 90 at the location identified by the pointer 94 in FIG. 9. In this way, a user can rapidly name structure and apply markers identifying that structure to the relevant parts of an image. As mentioned above, a geometric shape can be used as a marker. This finds particular application when a sonographer notices a diagnostic region of interest that a physician should review but does not wish to alarm the patient. In this case, the sonographer can position the pointer 94 over a location of the ultrasound image (as shown in FIG. 10) and issue a voiced command, such as "rectangle." This voiced command results in a rectangle 96 displayed on the image 90, as shown in FIG. 11.

In the embodiment describe above, a user first positioned a pointer over an ultrasound image, and the marker was placed on the image at the location identified by the pointer. In an alternate embodiment, the marker that is displayed on the ultrasound image can be positioned by the user with a pointing device such as a mouse. Pressing the mouse button would pin the marker in place. Further, a voiced command can be converted into a plurality of markers that are each positioned by the user. For example, if the user says "tumors," multiple "tumor" markers are displayed. The user then can use a pointing device to drag and drop each marker at the appropriate location on the image. Additionally, the user can position the pointer over a displayed marker and voice a command to copy or delete the marker.

Figure 12:
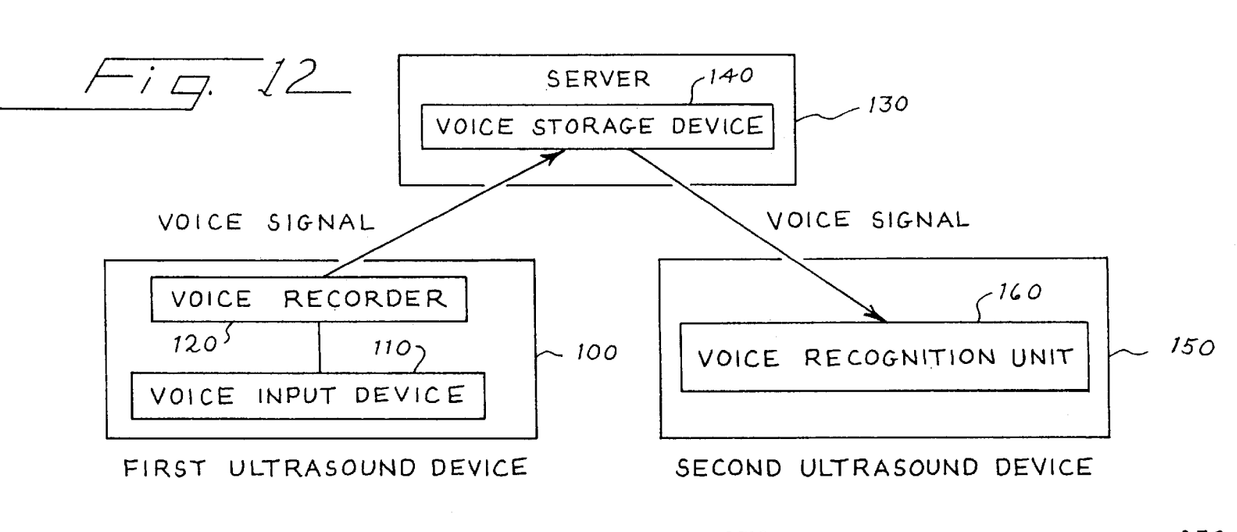
FIG. 12 is a block diagram of a network arrangement of a preferred embodiment.

In another preferred embodiment shown in FIG. 12, a first ultrasound device 100 comprising a voice input device 110 and a voice recorder 120 is coupled with a server 130 comprising a voice storage device 140. The server 130 is also coupled with a second ultrasound device 150 comprising a voice recognition unit 160. As used in this preferred embodiment and those described below, the term "ultrasound device" is intended to define either an ultrasound imaging system or an ultrasound review station. For example, in the embodiment shown in FIG. 12, the first ultrasound device 100 can be an ultrasound imaging system, and the second ultrasound device 150 can be an ultrasound review station.

Figure 13:
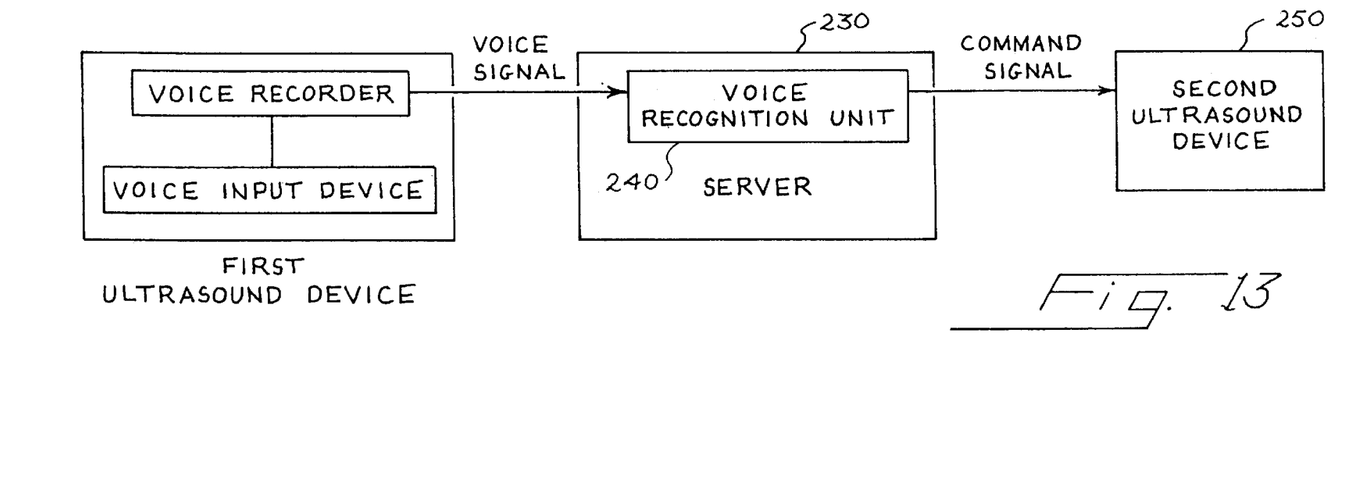
FIG. 13 is a block diagram of another network arrangement of a preferred embodiment.

With the network relationship shown in FIG. 12, voice signals provided to the voice input device 110 of the first ultrasound device 100 are converted into digital form by the voice recorder 120 and are transmitted for storage in the voice storage device 140 of the server 130. These stored voice signals can then be transmitted to the second ultrasound device 150 for conversion by its voice recognition unit 160. In one alternate embodiment, instead of using a network relationship, voice signals can be transferred from the first ultrasound device 100 via a portable storage device, such as a magneto-optical disc, or via a communication link (such as a cable) directly coupling the first and second ultrasound devices 100, 150. In another alternate embodiment shown in FIG. 13, the server 230 has a voice recognition unit 240 and supplies the second ultrasound device 250 with a command signal instead of a voice signal. In yet another alternate embodiment, the server 230 provide several ultrasound devices in the ultrasound network with the command signal. This is particularly useful in teaching environments, in which the command signal can be used to control several devices on the network. Also, the first and second ultrasound devices can be the same device, such as when an ultrasound imaging system provides voiced commands to the server, and the server returns command signals to the ultrasound imaging system.

These preferred embodiments are particularly useful when the first ultrasound device is an ultrasound imaging system and the second ultrasound device is an ultrasound review station. After an ultrasound examination is performed with the ultrasound imaging system, a user can dictate information into the voice input device for a report to be generated for the examination on the review station. The dictated information is recorded by a voice recorder of the ultrasound examination system, and the voice data is provided to the ultrasound imaging system via the server or portable storage device. The voice recognition unit of the server or ultrasound review station transcribes the voice data and inserts the transcription into an ultrasound examination report. The above-described embodiments associated with generating an ultrasound examination report can be used to enhance recognition. For example, in dictating a Normal OB report, the user can utter: "Diagnosis section: Normal diagnosis". On conversion, the command "normal diagnosis" would be trigger a macro to provide a textual phrase in the diagnosis section of a Normal OB report.

Voice Feedback

Figure 14:
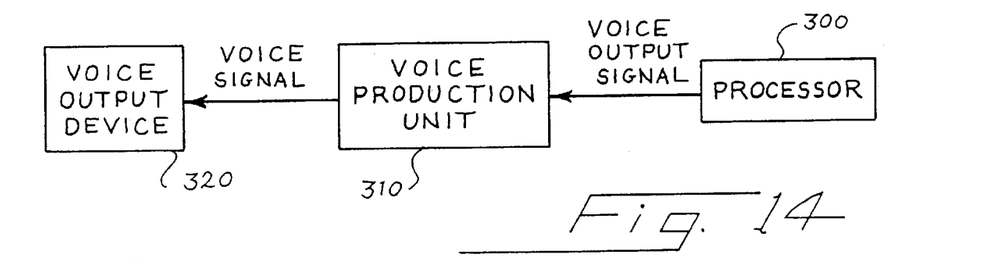
FIG. 14 is a block diagram illustrating an operation of a voice production unit of a preferred embodiment.

A voice production unit can be used with to provide voice feedback with an ultrasound imaging system or review station, and FIG. 14 provides a block diagram of a voice production unit 310 of a preferred embodiment. As shown in FIG. 14, the voice production unit 310 is coupled with a voice output device 320 (such a speaker) and a processor 300 of an ultrasound imaging system or review station. As with the voice recognition unit, the voice production unit 310 can comprise hardware and/or software components. A suitable voice production unit 310 can be purchased from Dragon Systems, Elan Informatique, IBM, Microsoft, Eloquent, Lernout & Hasupie, and AcuVoice. The voice production unit 310 can generate a synthesized or prerecorded voice. In operation, the processor 300 provides the voice production unit 310 with a voice output signal. The voice production unit 310 converts this signal to a voice signal and provides the voice signal to the voice output device 320.

With a voice production unit 310, an ultrasound imaging system or review station can bring information to the user's attention using voice feedback instead of or along with displaying such information visually. In this way, the ultrasound imaging system or review station can communicate with a user without cluttering a display screen. Additionally, voice feedback can be used to provide the user with information that is of interest but not important enough to merit distracting the user by presenting it visually. In this way the information can be provided to the user as background audio, which the user can choose to ignore. The voice production unit can be used with or integrated with a voice recognition unit, such as when the voice production unit and the voice recognition unit share some or all or its hardware and/or software components. An ultrasound imaging system or review station using both a voice recognition unit and a voice production unit can provide a fluid voice environment. For example, voice feedback can be used to confirm an action ("Are-you-sure?") and can also be used to reply to a voiced request (e.g., User asks, "Is the study in room 10 done? and the system responds in voice, "The study is complete and prior studies are being obtained"). The voice production unit can also be used to provide verbal alerts, the status of a voice recognition unit, and an indication of a completion of an activity. To avoid interruptions, the user can also command the system not to provide voice feedback.

Voice-Related User Interfaces

Figure 15:
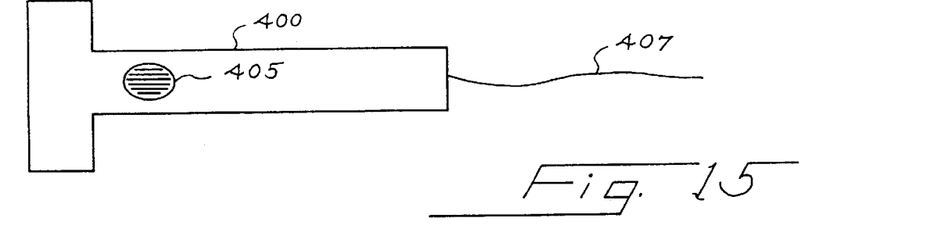
FIG. 15 is an illustration of a preferred transducer having a built-in microphone.
Figure 16:
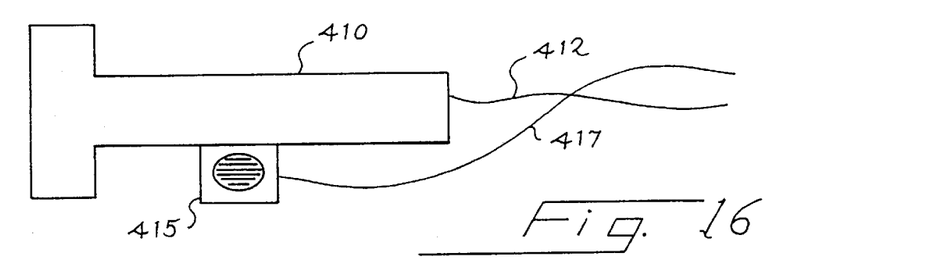
FIG. 16 is an illustration of a preferred transducer having an attached microphone.

There are several voice-related user interfaces that can be used with an ultrasound imaging system or review station. A user can issue voiced commands to an ultrasound imaging system or review station via a headset, a wireless microphone (such as a microphone manufactured by Shure), an attached microphone, or an array microphone. To allow a user to work closer to a patient, the ultrasound transducer shown in FIGS. 15 and 16 can be used. FIG. 15 is an illustration of a preferred ultrasound transducer 400. This ultrasound transducer 400 has at least one transducer element and a microphone 405. Both the transducer element(s) and microphone 405 provide electrical signals to an ultrasound imaging system coupled with the ultrasound transducer 400. In the transducer 400 shown in FIG. 15, the microphone 405 is built-into the transducer 400, and a single electrical connector 407 carries the electrical signals from the transducer element(s) and the microphone 405 to the ultrasound imaging system. In FIG. 16, the microphone 415 is added onto the transducer 410 as a removably-coupled component, which has an electrical connector 417 that is separate from the connector 412 used to carry electrical signals from the transducer element(s), although any appropriate number of connectors (including a single connector) can be used.

Figure 17:
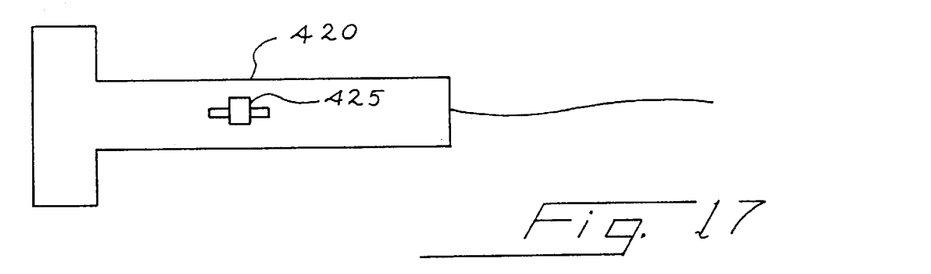
FIG. 17 is an illustration of a preferred transducer having a built-in slider.
Figure 18:
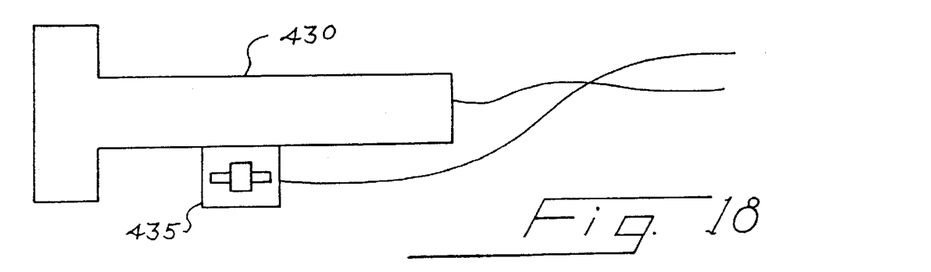
FIG. 18 is an illustration of a preferred transducer having an attached slider.

In another preferred embodiment, voice commands can be used to assign a function to a user interface device built into or attached to an ultrasound imaging system or ultrasound review station. The user interface device can take any suitable form (such as, but not limited to, a wheel, button, trackball, slider, and knob) attached directly or indirectly to the ultrasound imaging system or review station. For example, the user interface can be a pre-existing button on an ultrasound review station keyboard or a specially-designed knob added to an ultrasound imaging system. The user interface device can also be part of or attached to an ultrasound transducer. For example, FIG. 17 is an illustration of an ultrasound transducer 420 with a built-in slider 425, and FIG. 18 is an illustration of an ultrasound transducer 430 with a removably-attached slider 435. Although two separate electrical connectors are shown in FIG. 17, a single connector can be used. With the user interface device on the transducer, continuous or button-type controls previously located at the ultrasound imaging system can be manipulated at a distance.

Figure 19:
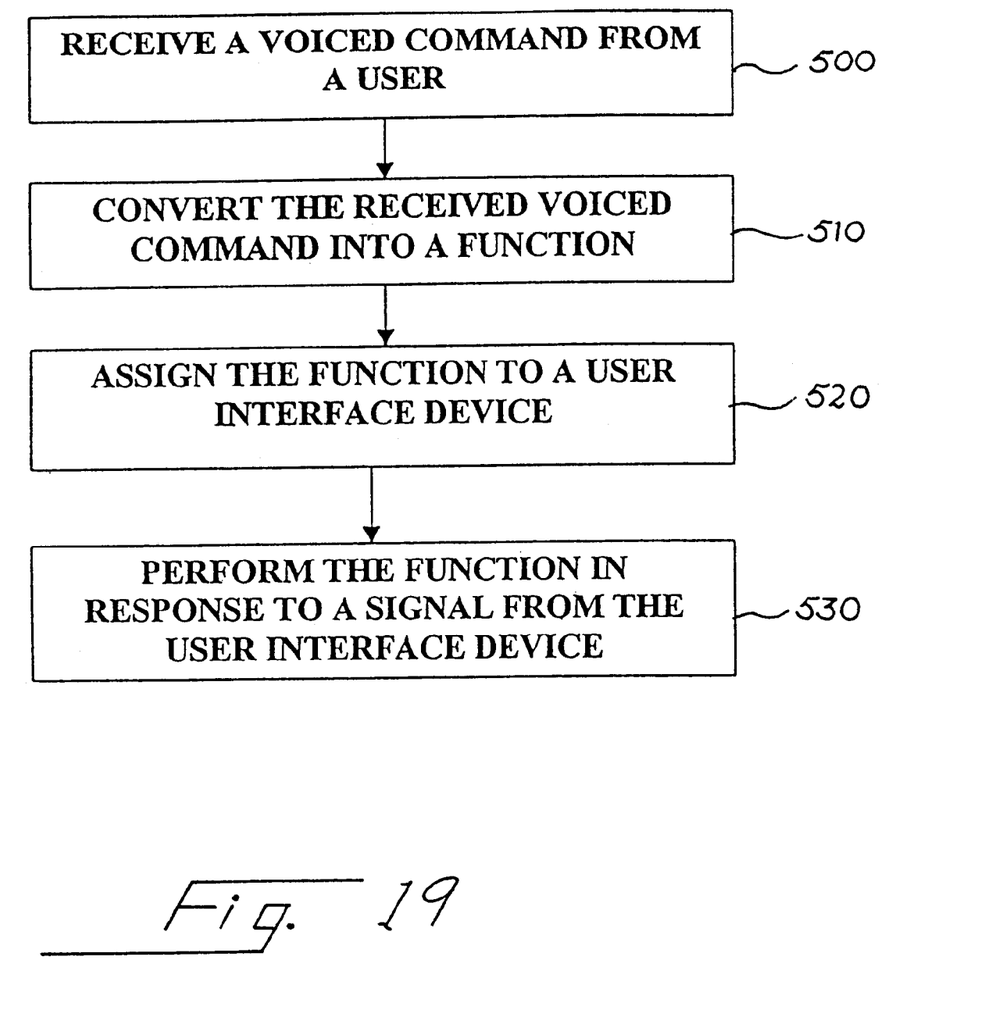
FIG. 19 is a flow chart of a preferred method for using voice commands to assign a function to an ultrasound imaging system or ultrasound review station user interface.

FIG. 19 is a flow chart of a preferred method for using voice commands to assign a function to an ultrasound imaging system or ultrasound review station user interface. First, a voiced command from the user is received (500). This voiced command is converted into a function (510), and the function is assigned to a user interface device (520). When the user manipulates the user interface device causing it to transmit a signal to the processor of the ultrasound imaging system or review station, the assigned function is performed (530).

With these preferred embodiments, the function of a user interface device can be easily changed by voice, such as when an ultrasound transducer has both a built-in depressible wheel and an attached microphone. As a user is performing an ultrasound examination, he speaks the word "gain" into the microphone of the ultrasound transducer. The ultrasound imaging system would then assign the gain function to the wheel. When the user scrolls the wheel forward, the ultrasound imaging system would increase the gain, and when the user scrolls the wheel backwards, the ultrasound imaging system would decrease the gain. If the user then says "image," an image would be generated when the user presses the depressible wheel. In this way, by issuing simple voice commands, the user can control a variety of functions with a single user interface device. Of course multiple user interface devices can be used in combination.

Appendix A provides further details of a presently preferred embodiment. Additionally, while the above-preferred embodiments were described above with respect to an ultrasound review station, review stations for use with other imaging modalities can be used.

The foregoing detailed description has described only a few of the many forms that this invention can take. Of course, many changes and modifications are possible to the preferred embodiments described above. For this reason it is intended that this detailed description be regarded as an illustration and not as a limitation of the invention. It is only the following claims, including all equivalents, that are intended to define the scope of this invention.

What is claimed is:

1. An ultrasound review station comprising:
   a voice input device;
   a processor; and
   a voice recognition unit coupled with the voice input device and processor, the voice recognition unit being operative to convert a voice signal received from the voice input device into a command signal recognizable by the processor;
   wherein the processor is operative to provide the voice recognition unit with voice information correlating a set of command signals recognizable by the processor-with an associated set of respective voice signals.

2. The ultrasound review station of claim 1, wherein the command signal instructs the processor to display an ultrasound image.

3. The ultrasound review station of claim 1, wherein the command signal instructs the processor to display an ultrasound examination report.

4. The ultrasound review station of claim 1, wherein the command signal instructs the processor to insert a textual phrase into an ultrasound examination report.

5. The ultrasound review station of claim 1, wherein the command signal instructs the processor to insert an ultrasound image into an ultrasound examination report.

6. The ultrasound review station of claim 1, wherein the command signal instructs the processor to perform an editing operation within an ultrasound examination report.

7. The ultrasound review station of claim 1, wherein the command signal instructs the processor to navigate through displayed information.

8. The ultrasound review station of claim 1, wherein the command signal instructs the processor to display a marker on an ultrasound image.

9. The ultrasound review station of claim 1 further comprising a display device coupled with the processor, and wherein the command signal instructs the processor to display available voice commands on the display device.

10. The ultrasound review station of claim 1, wherein the command signal selects a focus.

11. The ultrasound review station of claim 1 further comprising a plurality of display devices coupled with the processor, and wherein the command signal instructs the processor to select one of said plurality of display devices.

12. The ultrasound review station of claim 1 further comprising.
   a voice output device; and
   a voice production unit coupled with the processor and the voice output device, the voice production unit being operative to convert a voice output signal from the processor into a voice reproducible by the voice output device.

13. The ultrasound review station of claim 12, wherein the voice recognition unit and the voice production unit are integrated.

14. An ultrasound review station comprising:
   a voice output device;
   a processor;
   a voice production unit coupled with the processor and the voice output device, the voice production unit being operative to convert a voice output signal from the processor into a voice reproducible by the voice output device;
   a voice input device; and
   a voice recognition unit coupled with the voice input device and processor, the voice recognition unit being operative to convert a voice signal received from the voice input device into a command signal recognizable by the processor.

15. The ultrasound review station of claim 14, wherein the voice reproducible by the voice output device asks the user to confirm a command.

16. The ultrasound review station of claim 14, wherein the voice reproducible by the voice output device provides the user with a verbal alert.

17. The ultrasound review station of claim 14, wherein the voice reproducible by the voice output device provides an answer to a query presented to the processor by a user.

18. The ultrasound review station of claim 14, wherein the voice reproducible by the voice output device provides the user a status of a voice recognition unit.

19. The ultrasound review station of claim 14, wherein the voice reproducible by the voice output device provides an indication of a completion of an activity.

20. The ultrasound review station of claim 14, wherein the voice recognition unit and the voice production unit are integrated.

21. An ultrasound imaging system comprising;
   a processor;
   a voice output device;
   a voice production unit coupled with the processor and the voice output device, the voice production unit being operative to convert a voice output signal from the processor into a voice reproducible by the voice output device;
   a voice input device; and
   a voice recognition unit coupled with the voice input device and processor, the voice recognition unit being operative to convert a voice signal received from the voice input device into a command signal recognizable by the processor.

22. The ultrasound imaging system of claim 21, wherein the voice reproducible by the voice output device asks the user to confirm a command.

23. The ultrasound imaging system of claim 21, wherein the voice reproducible by the voice output device provides the user with a verbal alert.

24. The ultrasound imaging system of claim 21, wherein the voice reproducible by the voice output device provides an answer to a query presented to the processor by a user.

25. The ultrasound imaging system of claim 21, wherein the voice reproducible by the voice output device provides the user with a status of a voice recognition unit.

26. The ultrasound imaging system of claim 21, wherein the voice reproducible by the voice output device provides an indication of a completion of an activity.

27. The ultrasound imaging system of claim 21, wherein the voice recognition unit and the voice production unit are integrated.

28. A method for converting a received voiced command into a command signal recognizable by an ultrasound imaging system processor, the method comprising:
   (a) with an ultrasound imaging system processor, providing a voice recognition unit with voice information correlating a set of command signals recognizable by the ultrasound imaging system processor with an associated set of respective voiced commands;
   (b) with the voice recognition unit, receiving a voiced command; and
   (c) converting the received voiced command into a command signal using the voice information provided by the ultrasound imaging system processor.

29. The method of claim 28 further comprising:

(d) with the voice recognition unit, providing the command signal to the ultrasound imaging system processor.

30. A method for converting a received voiced command into a command signal recognizable by an ultrasound review station processor, the method comprising:

(a) with an ultrasound review station processor, providing a voice recognition unit with voice information correlating a set of command signals recognizable by the ultrasound review station processor with an associated set of respective voiced commands;

(b) with the voice recognition unit, receiving a voiced command; and (c) converting the received voiced command into a command signal using the voice information provided by the ultrasound review station processor.

31. The method of claim 30 further comprising:

(d) with the voice recognition unit, providing the command signal to the ultrasound review station processor.

32. An ultrasound transducer comprising:

at least one transducer element; and a microphone for receiving voice input, wherein said input is being part of the ultrasound transducer;

said at least one transducer element and said microphone providing electrical signals to an ultrasound imaging system coupled with the ultrasound transducer.

33. The ultrasound transducer of claim 32, wherein the microphone is built-into the ultrasound transducer.

34. The ultrasound transducer of claim 32, wherein the microphone is removeably coupled with the ultrasound transducer.

\* \* \* \* \*